United States Patent
Koseoglu et al.

(10) Patent No.: US 11,236,031 B2
(45) Date of Patent: Feb. 1, 2022

(54) INTEGRATED PROCESS FOR THE PRODUCTION OF ISONONANOL AND GASOLINE AND DIESEL BLENDING COMPONENTS

(71) Applicant: Saudi Arabian Oil Company, Dhahran (SA)

(72) Inventors: Omer Refa Koseoglu, Dhahran (SA); Sohel Shaikh, Dhahran (SA); Zhonglin Zhang, Dhahran (SA); Salem R. AlSubayee, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 47 days.

(21) Appl. No.: 16/789,092

(22) Filed: Feb. 12, 2020

(65) Prior Publication Data
US 2021/0253504 A1    Aug. 19, 2021

(51) Int. Cl.
*C07C 29/141* (2006.01)
*C07C 41/06* (2006.01)
(Continued)

(52) U.S. Cl.
CPC ........... *C07C 29/141* (2013.01); *B01J 19/245* (2013.01); *C07C 2/08* (2013.01); *C07C 2/864* (2013.01);
(Continued)

(58) Field of Classification Search
CPC ..... C07C 29/141; C07C 45/505; C07C 45/50; C07C 43/046; C07C 2/864; C07C 41/06;
(Continued)

(56) References Cited

U.S. PATENT DOCUMENTS

| | | | |
|---|---|---|---|
| 5,864,052 A | * | 1/1999 | Nierlich ................... C07C 11/02 568/697 |
| 5,912,191 A | * | 6/1999 | Nierlich ................... C07C 11/02 44/449 |

(Continued)

FOREIGN PATENT DOCUMENTS

| | | |
|---|---|---|
| EP | 3693356 A1 | 8/2020 |
| WO | 2017146876 A1 | 8/2017 |
| WO | 2019021257 A1 | 1/2019 |

OTHER PUBLICATIONS

International Search Report and Written Opinion in Corresponding PCT Application No. PCT/US2021/017524 dated May 12, 2021. 13 pages.

*Primary Examiner* — Ali Z Fadhel
(74) *Attorney, Agent, or Firm* — Leason Ellis LLP

(57) ABSTRACT

The present application provides systems and methods for producing isononanol and gasoline and diesel blending components. In at least one embodiment of the present systems and methods, a hydrocarbon feed is cracked in a steam cracker to form a first ethylene stream, a first propylene stream, and a C4 stream comprising isobutene and butadiene. The C4 stream is reacted with a methanol stream in a methyl tertiary butyl ether (MTBE) unit to form MTBE and a butadiene-rich C4 stream. The butadiene-rich C4 stream is selectively hydrogenated in a butadiene unit to form a butene-rich C4 stream. The butene-rich C4 stream undergoes a series of reactions in an isononanol unit to produce isononanol and an olefin-rich stream. The olefin-rich stream is then separate, in a separation unit, a C8, C12, and C16 fuel oil streams.

10 Claims, 9 Drawing Sheets

| | Products | | Delta |
|---|---|---|---|
| | Prior Art FIG. 1 | Embodiment of FIG. 3 | |
| | KTA | KTA | KTA |
| MTBE | 342 | 344 | |
| 1,3-butadiene | 402 | | |
| INA | 158 | 588 | 430 |
| | | | |
| Low value C8-C16 mix stream (Total) | 42 | 147 | 105 |
| C8 Gasoline blending | | 36 | |
| C12, Diesel blending | | 82 | |
| C16, Diesel blending | | 29 | |

(51) Int. Cl.
| | |
|---|---|
| C07C 5/05 | (2006.01) |
| C07C 6/04 | (2006.01) |
| C07C 5/03 | (2006.01) |
| C07C 45/34 | (2006.01) |
| C07C 2/08 | (2006.01) |
| B01J 19/24 | (2006.01) |
| C10L 1/06 | (2006.01) |
| C10L 1/08 | (2006.01) |
| C10L 1/16 | (2006.01) |
| C10G 9/36 | (2006.01) |
| C07C 2/86 | (2006.01) |
| C07C 43/04 | (2006.01) |
| C07C 45/50 | (2006.01) |
| C07C 41/08 | (2006.01) |
| C07C 4/04 | (2006.01) |
| C07C 4/02 | (2006.01) |
| C07C 29/14 | (2006.01) |
| C07C 29/136 | (2006.01) |
| C07C 45/49 | (2006.01) |
| C07C 6/06 | (2006.01) |
| C07C 1/24 | (2006.01) |

(52) U.S. Cl.
CPC ............... *C07C 5/03* (2013.01); *C07C 5/05* (2013.01); *C07C 6/04* (2013.01); *C07C 41/06* (2013.01); *C07C 43/046* (2013.01); *C07C 45/34* (2013.01); *C07C 45/50* (2013.01); *C07C 45/505* (2013.01); *C10G 9/36* (2013.01); *C10L 1/06* (2013.01); *C10L 1/08* (2013.01); *C10L 1/1608* (2013.01); *B01J 2219/0004* (2013.01); *B01J 2231/321* (2013.01); *C07C 1/24* (2013.01); *C07C 2/86* (2013.01); *C07C 2/862* (2013.01); *C07C 4/02* (2013.01); *C07C 4/04* (2013.01); *C07C 6/06* (2013.01); *C07C 29/136* (2013.01); *C07C 29/14* (2013.01); *C07C 41/08* (2013.01); *C07C 45/49* (2013.01); *C10G 2300/1044* (2013.01); *C10G 2300/1088* (2013.01); *C10G 2300/1092* (2013.01); *C10G 2400/02* (2013.01); *C10G 2400/04* (2013.01); *C10G 2400/22* (2013.01); *C10L 2270/023* (2013.01); *C10L 2270/026* (2013.01); *C10L 2290/544* (2013.01)

(58) Field of Classification Search
CPC .... C07C 2/08; C07C 6/04; C07C 5/05; C07C 45/34; C07C 5/03; C07C 6/06; C07C 1/24; C07C 45/49; C07C 29/136; C07C 29/14; C07C 4/02; C07C 4/04; C07C 2/862; C07C 41/08; C07C 2/86; B01J 19/245; B01J 2231/321; B01J 2219/0004; C10L 1/1608; C10L 1/08; C10L 1/06; C10L 2290/544; C10L 2270/026; C10L 2270/023; C10G 9/36; C10G 2300/1088; C10G 2400/04; C10G 2400/22; C10G 2400/02; C10G 2300/1092; C10G 2300/1044

See application file for complete search history.

(56) References Cited

U.S. PATENT DOCUMENTS

| | | |
|---|---|---|
| 6,403,840 B1 | 6/2002 | Zhou et al. |
| 6,447,558 B1 | 9/2002 | Yeh et al. |
| 7,437,812 B2 | 10/2008 | Baird |
| 8,153,851 B2 | 4/2012 | Gartside et al. |
| 9,365,715 B2 | 6/2016 | Knoll et al. |
| 9,834,497 B2 | 12/2017 | Shaikh et al. |
| 9,914,681 B2 | 3/2018 | Geilen et al. |
| 10,059,645 B2 | 8/2018 | Shaikh et al. |
| 10,214,466 B2 | 2/2019 | Shaikh et al. |
| 2006/0100473 A1* | 5/2006 | Grootjans ............... C10G 11/05 585/652 |
| 2007/0135665 A1* | 6/2007 | Wiese ....................... C07C 6/04 585/16 |
| 2009/0312583 A1* | 12/2009 | Sigi ........................ C07C 29/141 568/909 |
| 2010/0048959 A1* | 2/2010 | Sigi ........................ C07C 45/74 568/450 |
| 2013/0158321 A1 | 6/2013 | Olivier-Bourbigou et al. |
| 2015/0191410 A1* | 7/2015 | Frey ........................ C07C 51/56 549/515 |
| 2018/0072647 A1* | 3/2018 | Stochniol ................. C07C 2/24 |

* cited by examiner

PRIOR ART

FIG. 5A

| Component | Typical Composition W% | This Example W% |
|---|---|---|
| 1,3-butadiene | 35-50 | 41 |
| i-butene | 15-30 | 22 |
| cis-butene-2 | 5-10 | 8 |
| trans-butene-2 | 5-10 | 7 |
| butene-1 | 5-20 | 11 |
| i-butane | 1-5 | 4 |
| n-butane | 1-10 | 7 |
| TOTAL | 100 | 100 |

FIG. 5B

| | Products | | |
|---|---|---|---|
| | Prior Art FIG. 1 | Embodiment of FIG. 3 | Delta |
| | KTA | KTA | KTA |
| MTBE | 342 | 344 | |
| 1,3-butadiene | 402 | | |
| INA | 158 | 588 | 430 |
| Low value C8-C16 mix stream (Total) | 42 | 147 | 105 |
| C8 Gasoline blending | | 36 | |
| C12, Diesel blending | | 82 | |
| C16, Diesel blending | | 29 | |

Streams for Prior Art System – FIG. 1

FIG. 6

| Conduit # | 5 | 6 | 7 | 8 | 9 | 10 | 11 | 12 | 13 |
|---|---|---|---|---|---|---|---|---|---|
| H2 | 0 | 0 | 0 | 0 | 0 | 0 | 0 | 0 | 0 |
| MeOH | 0 | 0 | 0 | 125 | 0 | 0 | 0 | 0 | 0 |
| MTBE | 0 | 0 | 0 | 0 | 342 | 0 | 0 | 0 | 0 |
| 1,3-butadiene | 410 | 410 | 0 | 0 | 0 | 0 | 0 | 0 | 0 |
| i-butene | 220 | 0 | 220 | 0 | 0 | 0 | 0 | 0 | 0 |
| cis-butene-2 | 80 | 0 | 80 | 0 | 0 | 80 | 0 | 0 | 13 |
| trans-butene-2 | 70 | 0 | 70 | 0 | 0 | 70 | 0 | 0 | 12 |
| butene-1 | 110 | 0 | 110 | 0 | 0 | 110 | 0 | 0 | 41 |
| i-butane | 40 | 0 | 40 | 0 | 0 | 40 | 0 | 0 | 47 |
| n-Butane | 70 | 0 | 70 | 0 | 0 | 70 | 0 | 0 | 81 |
| INA | 0 | 0 | 0 | 0 | 0 | 0 | 158 | 0 | 0 |
| C8 | 0 | 0 | 0 | 0 | 0 | 0 | 0 | 10 | 0 |
| C12 | 0 | 0 | 0 | 0 | 0 | 0 | 0 | 23 | 0 |
| C16 | 0 | 0 | 0 | 0 | 0 | 0 | 0 | 8 | 0 |
| Total | 1000 | 410 | 590 | 125 | 342 | 370 | 158 | 41 | 193 |

Streams for Embodiment of FIG. 2

| Conduit # | 218 | 220 | 222 | 224 | 226 | 228 | 230 | 234 | 236 - 240 |
|---|---|---|---|---|---|---|---|---|---|
| H2 | 0 | 0 | 0 | 0 | 0 | 0 | 0 | 0 | 0 |
| MeOH | 0 | 125 | 0 | 0 | 0 | 0 | 0 | 0 | 0 |
| MTBE | 0 | 0 | 344 | 0 | 0 | 0 | 0 | 0 | 0 |
| 1,3- butadiene | 410 | 0 | 0 | 410 | 410 | 0 | 0 | 0 | 0 |
| i-butene | 220 | 0 | 0 | 0 | 0 | 0 | 0 | 0 | 0 |
| cis-butene-2 | 80 | 0 | 0 | 80 | 0 | 80 | 0 | 13 | 0 |
| trans-butene-2 | 70 | 0 | 0 | 70 | 0 | 70 | 0 | 12 | 0 |
| butene-1 | 110 | 0 | 0 | 110 | 0 | 110 | 0 | 41 | 0 |
| i-butane | 40 | 0 | 0 | 40 | 0 | 40 | 0 | 47 | 0 |
| n-butane | 70 | 0 | 0 | 70 | 0 | 70 | 0 | 81 | 0 |
| INA | 0 | 0 | 0 | 0 | 0 | 0 | 158 | 0 | 0 |
| C8 | 0 | 0 | 0 | 0 | 0 | 0 | 0 | 0 | 10 |
| C12 | 0 | 0 | 0 | 0 | 0 | 0 | 0 | 0 | 23 |
| C16 | 0 | 0 | 0 | 0 | 0 | 0 | 0 | 0 | 8 |
| Total | 1000 | 125 | 344 | 780 | 410 | 370 | 158 | 193 | 41 |

FIG. 7

Streams for Embodiment of FIG. 3

| Conduit # | 218 | 220 | 222 | 224 | 226 | 228 | 230 | 234 | 236 - 240 |
|---|---|---|---|---|---|---|---|---|---|
| H2 | 0 | 0 | 0 | 0 | 15 | 0 | 0 | 0 | 0 |
| MeOH | 0 | 125 | 0 | 0 | 0 | 0 | 0 | 0 | 0 |
| MTBE | 0 | 0 | 344 | 0 | 0 | 0 | 0 | 0 | 0 |
| 1,3- butadiene | 410 | 0 | 0 | 410 | 0 | 0 | 0 | 0 | 0 |
| i-butene | 220 | 0 | 0 | 0 | 0 | 0 | 0 | 0 | 0 |
| cis-butene-2 | 80 | 0 | 0 | 80 | 0 | 143 | 0 | 14 | 0 |
| trans-butene-2 | 70 | 0 | 0 | 70 | 0 | 127 | 0 | 13 | 0 |
| butene-1 | 110 | 0 | 0 | 110 | 0 | 413 | 0 | 44 | 0 |
| i-butane | 40 | 0 | 0 | 40 | 0 | 40 | 0 | 51 | 0 |
| n-butane | 70 | 0 | 0 | 70 | 0 | 72 | 0 | 87 | 0 |
| INA | 0 | 0 | 0 | 0 | 0 | 0 | 558 | 0 | 0 |
| C8 | 0 | 0 | 0 | 0 | 0 | 0 | 0 | 0 | 36 |
| C12 | 0 | 0 | 0 | 0 | 0 | 0 | 0 | 0 | 82 |
| C16 | 0 | 0 | 0 | 0 | 0 | 0 | 0 | 0 | 29 |
| Total | 1000 | 125 | 344 | 780 | 15 | 795 | 558 | 209 | 147 |

FIG. 8

INTEGRATED PROCESS FOR THE PRODUCTION OF ISONONANOL AND GASOLINE AND DIESEL BLENDING COMPONENTS

TECHNICAL FIELD

The present disclosure is generally related to systems and processes for producing isononanol and gasoline components and more particularly related to integrated systems and processes for producing isononanol and gasoline blending components from a hydrocarbon feed.

BACKGROUND OF THE DISCLOSURE

Steam cracking is a petrochemical process in which a hydrocarbon feedstock (e.g., hydrogen rich paraffinic and naphthenic hydrocarbons) are converted into light olefins such as ethylene, propylene and butenes.

Oxo technology is a leading technology for the manufacture of oxo alcohols from olefins. This technology includes oxo alcohol production processes in which alcohols are produced at low pressure over homogeneous catalysts (e.g., rhodium) via hydroformylation reactions of an olefin with syngas (CO and $H_2$), followed by hydrogenation reactions of an intermediate aldehyde. For example, propylene can be hydroformylated to produce butyraldehyde and iso-butyraldehyde, which are then hydrogenated to produce normal butanol and iso-butanol respectively. The production of 2-ethylhexanol, for example, is achieved by aldolization of the normal-butyraldehyde followed by hydrogenation of the aldol intermediates. Isononanol (INA) has been produced via oxo processes from raffinate-2 streams, for example. Isononanol production capacity in these oxo processes, however, is limited by the amounts of butene-1 and butene-2 in the raffinate-2 stream.

While steam cracking and oxo processes are often utilized separately, these processes have not been integrated into a single system in an efficient and cost-effective manner.

The present application addresses these and other challenges related to related to steam cracking and oxo processes for the production of oxo alcohols.

SUMMARY OF THE DISCLOSURE

In a first aspect, a method for producing isononanol and gasoline and diesel blending components is provided. In the method, a hydrocarbon feed undergoes a cracking reaction in a steam cracker to form a first ethylene stream, a first propylene stream, and a C4 stream including isobutene and butadiene. The C4 stream is then reacted with a methanol stream in a methyl tertiary butyl ether (MTBE) unit to form MTBE and a butadiene-rich C4 stream. The butadiene-rich C4 stream is selectively hydrogenated in a butadiene unit to form a butene-rich C4 stream including butene-1, cis-butene-2, and trans-butene-2. The butene-rich C4 stream undergoes a series of reactions in an isononanol unit to produce isononanol and an olefin-rich stream. The olefin-rich stream is then separated in a separation unit into a C8 fuel oil stream, a C12 fuel oil stream, and a C16 fuel oil stream.

In another aspect, a first stream of unreacted C4 olefins from the butene-rich C4 stream is metathesized in a C4 metathesis unit to produce a second ethylene stream and a second propylene stream. A second stream of unreacted C4 olefins which is derived from the first stream of unreacted C4 olefins is then hydrogenated in a C4 hydrogenation unit to form butanes. In a further aspect, the second ethylene stream is combined with the first ethylene stream, and the second propylene stream is combined with the first propylene stream. In a further aspect, the butanes produced in the C4 hydrogenation unit are recycled to the steam cracker.

In another aspect, the series of reactions for producing isononanol and the olefin-rich stream include: dimerization and oligomerization of the butene-rich C4 stream to form butene dimers, including isooctene, and other C8, C12, and C16 components, which form the olefin-rich stream; hydroformylation of isooctene with syngas to form isononanal; and hydrogenation of isononanal to form isononanol.

In another aspect, the series of reactions for producing isononanol results in a stream of unreacted C4 olefins, and the stream of unreacted C4 olefins is recycled to the steam cracker.

In another aspect, the hydrocarbon feed comprises C1-C4 olefins and naphtha.

In a second aspect, another method for producing isononanol and gasoline and diesel blending components is provided. In the method, a hydrocarbon feed undergoes a cracking reaction in a steam cracker to form a first ethylene stream, a first propylene stream, and a C4 stream including isobutene and butadiene. The C4 stream is reacted with a methanol stream in an MTBE unit to form MTBE and a butadiene-rich C4 stream. Butadiene is then extracted from the butadiene-rich C4 stream in a butadiene unit, and the extraction of butadiene results in a butene-rich C4 stream including butene-1, cis-butene-2, and trans-butene-2. The butene-rich C4 stream undergoes a series of reactions in an isononanol unit to produce isononanol and an olefin-rich stream. The olefin-rich stream is separated in a separation unit into a C8 fuel oil stream, a C12 fuel oil stream, and a C16 fuel oil stream.

In another aspect, a first stream of unreacted C4 olefins from the butene-rich C4 stream is metathesized in a C4 metathesis unit to produce a second ethylene stream and a second propylene stream, and a second stream of unreacted C4 olefins is hydrogenated in a C4 hydrogenation unit to form butanes. The second stream of unreacted C4 olefins is derived from the first stream of unreacted C4 olefins. In a further aspect, the second ethylene stream is combined with the first ethylene stream and the second propylene stream is combined with the first propylene stream. In a further aspect, the butanes produced in the C4 hydrogenation unit are recycled to the steam cracker.

In another aspect, the series of reactions for producing isononanol and the olefin-rich stream includes: dimerization and oligomerization of the butene-rich C4 stream to form butene dimers including isooctene, and other C8, C12, and C16 components, which form the olefin-rich stream; hydroformylation of isooctene with syngas to form isononanal; and hydrogenation of isononanal to form isononanol.

In another aspect, the series of reactions for producing isononanol results in a stream of unreacted C4 olefins, and the stream of unreacted C4 olefins is recycled to the steam cracker.

In another aspect, the hydrocarbon feed comprises C1-C4 olefins and naphtha.

In a third aspect, a system for production of isononanol and gasoline and diesel blending components is provided. The system includes a steam cracker configured to receive a hydrocarbon feed. The hydrocarbon feed undergoes a cracking reaction in the steam cracker to form a first ethylene stream, a first propylene stream, and a C4 stream that includes isobutene and butadiene. The system also includes an MTBE unit fluidly connected to the steam cracker. The MTBE unit is configured to receive a methanol stream and to receive the C4 stream from the steam cracker. Isobutene in the C4 stream reacts with the received methanol in the MTBE unit to form MTBE, and the remaining C4 stream is a butadiene-rich C4 stream. The system includes a butadiene unit fluidly connected to the MTBE unit. The butadiene unit is configured to receive the butadiene-rich C4 stream from the MTBE unit. The butadiene-rich C4 stream is reacted in the butadiene unit to form a butene-rich C4 stream.

The system further includes an isononanol unit fluidly connected to the butadiene extraction unit. The isononanol unit is configured to receive the butene-rich C4 stream, and a portion of the butene-rich C4 stream undergoes a series of reactions to form an olefin-rich stream and an isononanol stream. The system also includes a separation unit fluidly connected to the isononanol unit. The separation unit is configured to receive the olefin-rich stream and in the separation unit, the olefin-rich stream is separated into a C8 fuel oil steam, a C12 fuel oil stream, and a C16 fuel oil stream.

In another aspect, the butadiene unit is a butadiene extraction unit, and the butadiene extraction unit is configured to separate butadiene from the butadiene-rich C4 stream to form the butene-rich C4 stream.

In another aspect, the butadiene unit is a butadiene selective hydrogenation unit. The butadiene selective hydrogenation unit is configured to receive a hydrogen stream, and in the butadiene selective hydrogenation unit, the butadiene-rich C4 stream undergoes a selective hydrogenation reaction with the hydrogen stream to form butene-1, cis-butene-2, and trans-butene-2. In a further aspect, the system includes a C4 metathesis unit. The C4 metathesis unit is configured to receive a stream of unreacted C4 olefins from the butene-rich C4 stream in the isononanol unit and a first portion of the stream of unreacted C4 olefins undergoes a metathesis reaction to produce a second ethylene stream and a second propylene stream. In this aspect, the system also includes a C4 hydrogenation unit configured to receive a second portion of the stream of unreacted C4 olefins from the C4 self-metathesis unit. The second portion of unreacted C4 olefins undergoes a hydrogenation reaction in the C4 hydrogenation unit to form butanes, and the C4 hydrogenation unit is configured to transfer the formed butanes back to the steam cracker. In a further aspect, the second ethylene stream is combined with the first ethylene stream via a first conduit and the second propylene stream is combined with the first propylene stream via a second conduit.

In another aspect, the series of reactions in the isononanol unit include dimerization and oligomerization of butenes to form butene dimers including isooctene, and other C8, C12, and C16 components, which form the olefin-rich stream; hydroformylation of isooctene with syngas to form isononanal; and hydrogenation of isononanal to form isononanol. In another aspect, the series of reactions in the isononanol unit result in a stream of unreacted C4 olefins, and the system further includes a recycling conduit configured to recycle the stream of unreacted C4 olefins to the steam cracker.

In another aspect, the first ethylene stream, the first propylene stream, and the C4 stream each exit the steam cracker via separate conduits. In another aspect, the hydrocarbon feed comprises C1-C4 olefins and naphtha.

BRIEF DESCRIPTION OF THE DRAWING FIGURES

FIG. 1 displays a high-level diagram which illustrates a prior art system for producing isononanol;

FIG. 2 shows a high-level diagram illustrating an integrated system for producing isononanol and gasoline and diesel blending components comprising a butadiene extraction unit in accordance with one or more embodiments; and FIG. 3 shows a high-level diagram illustrating an integrated system for producing isononanol and gasoline and diesel blending components comprising a butadiene selective hydrogenation unit in accordance with one or more embodiments; and FIG. 4 shows a high-level diagram illustrating an integrated system for producing isononanol and gasoline and diesel blending components comprising a C4 metathesis unit and C4 hydrogenation unit in accordance with one or more embodiments;

FIG. 5A shows an exemplary feedstock for the integrated system in accordance with one or more embodiments;

FIG. 5B shows the increased production of isononanol and C8-C16 fuel components provided by the present integrated system as compared to a convention system in accordance with one or more embodiments;

FIG. 6 shows an exemplary yield of various chemical species with a conventional isononanol production system;

FIG. 7 shows an exemplary yield of various chemical species with the present integrated system in accordance with one or more embodiments; and FIG. 8 shows an exemplary yield of various chemical species with the present integrated system in accordance with one or more embodiments.

DETAILED DESCRIPTION OF CERTAIN EMBODIMENTS IN ACCORDANCE WITH THE DISCLOSURE

In accordance with one or more embodiments, the present application discloses systems and methods for producing isononanol and gasoline and diesel blending components. In one or more embodiments, the system includes a steam cracker for cracking a hydrocarbon feed to form an ethylene stream, a propylene stream, and a C4 stream that comprises isobutene and butadiene. The system also includes a methyl tertiary butyl ether (MTBE) unit fluidly connected to the steam cracker. In the MTBE unit, the isobutene in the C4 stream reacts with a methanol stream to form MTBE and a butadiene-rich C4 stream.

The system further comprises a butadiene unit fluidly connected to the MTBE unit. In the butadiene unit, the butadiene-rich C4 stream is further reacted to form a butene-rich C4 stream. The butene-rich C4 stream is then transferred to an isononanol unit, where a portion of the butene-rich C4 stream undergoes a series of reactions to produce an olefin-rich stream and an isononanol stream. Finally, the system includes a separation unit fluidly connected to the isononanol unit, where the separation unit receives the olefin-rich stream and further separates it into gasoline and diesel blending components, including a C8 fuel oil steam, a C12 fuel oil stream, and a C16 fuel oil stream.

The present systems and methods result in a dramatic increase in the yield of isononanol relative to conventional systems and methods. The present systems and methods are also more cost-effective than existing systems and methods as a result of the separation of a low-value olefin-rich stream (C8-C16 components) into separated C8, C12, and C16 fuel oil streams, each of which can be utilized as valuable gasoline and/or diesel blending streams.

These and other aspects of the present methods are described in further detail below with reference to the accompanied drawing figures, in which one or more illustrated embodiments and/or arrangements of the systems and methods are shown. The systems and methods of the present application are not limited in any way to the illustrated embodiment and/or arrangement. It should be understood that the systems and methods as shown in the accompanying figures are merely exemplary of the systems and methods of the present application, which can be embodied in various forms as appreciated by one skilled in the art. Therefore, it is to be understood that any structural and functional details disclosed herein are not to be interpreted as limiting the present systems and methods, but rather are provided as a representative embodiment and/or arrangement for teaching one skilled in the art one or more ways to implement the present systems and methods.

Figure 1:
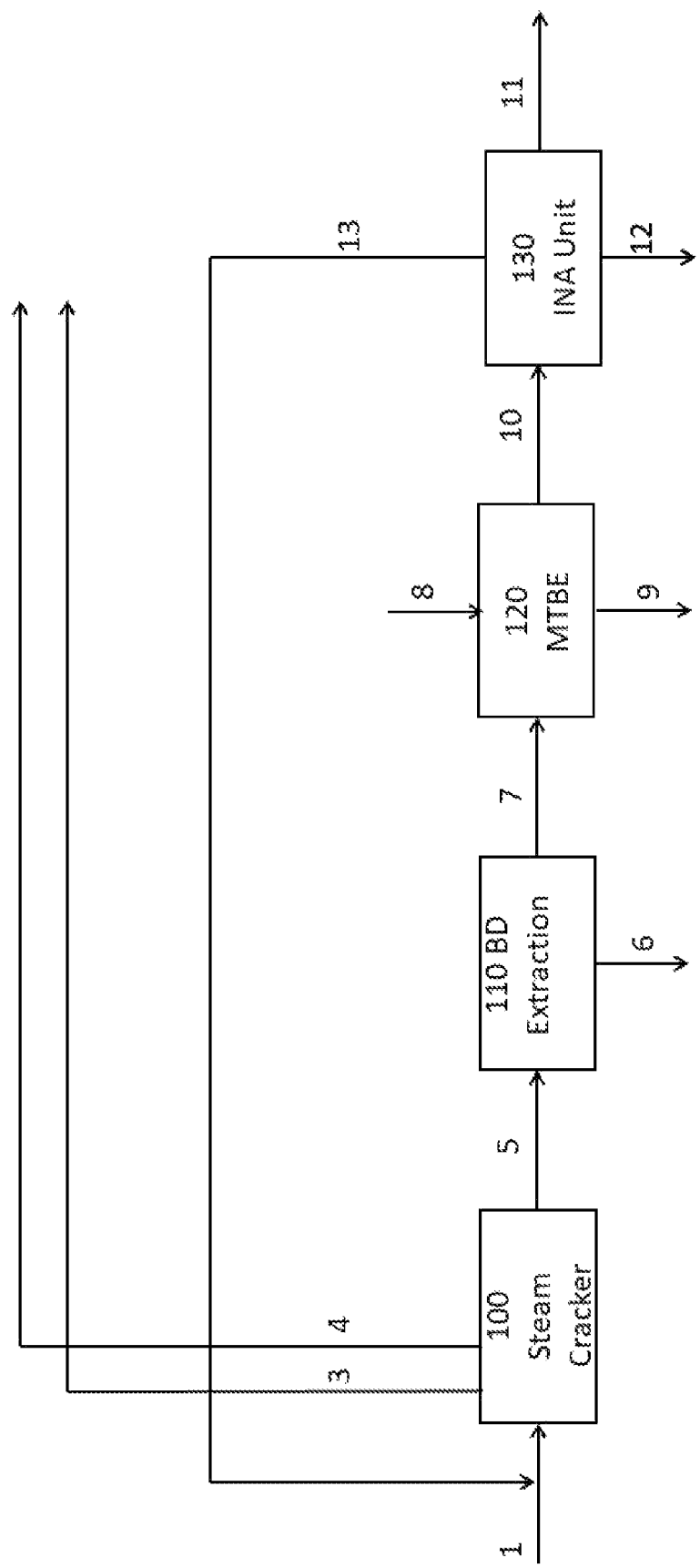

FIG. 1 displays a high-level diagram which illustrates a prior art system for producing isononanol. The prior art system includes a steam cracker 100, a butadiene extraction unit 110, a methyl tertiary butyl ether (MTBE) unit 120, and a isononanol unit 130. In the system of FIG. 1, a hydrocarbon feed (conduit 1), including C1-C4 hydrocarbons and naphtha, is fed to the steam cracker 100. In the steam cracker 100, the hydrocarbon feed is cracked to form an ethylene stream (conduit 3), a propylene stream (conduit 4), and a C4 stream (conduit 5). The C4 stream is then fed to the butadiene extraction unit 110, where butadiene is extracted from the C4 stream (conduit 6) and the remaining C4 stream is a butenes-rich C4 stream. The butenes-rich C4 stream (conduit 7) is then transferred to the MTBE unit 120, where the butenes-rich C4 stream is reacted with a methanol stream (conduit 8) to form MTBE (conduit 9).

The remaining butenes-rich C4 stream (conduit 10) is then fed from the MTBE unit 120 to the isononanol unit 130. In the isononanol unit 130, the butenes-rich C4 stream undergoes a series of reactions resulting in an isononanol stream (conduit 11) and an olefin-rich stream (conduit 12), along with any unreacted portions of the C4 stream (conduit 13). Typically, isononanol is produced from a butenes-rich C4 stream such as a raffinate-2 stream, which contains approximately 65% butenes and 35% butane. The production of isononanol is limited by the butenes content in the raffinate-2 stream. The by-product of the isononanol unit 130 is an olefin-rich stream that mainly comprises C4, C8, C12 and C16 hydrocarbons. The resulting olefin-rich stream is generally of low value on its own. Unreacted portions of the C4 stream (conduit 13) can be recycled from the isononanol unit 130 back to the steam cracker 100.

The systems of the present application utilize different configurations relative to the system shown in FIG. 1, resulting in substantial increase in the production of isononanol and improved utilization of the olefin-rich stream via separation into valuable gasoline and diesel blending streams.

Figure 2:
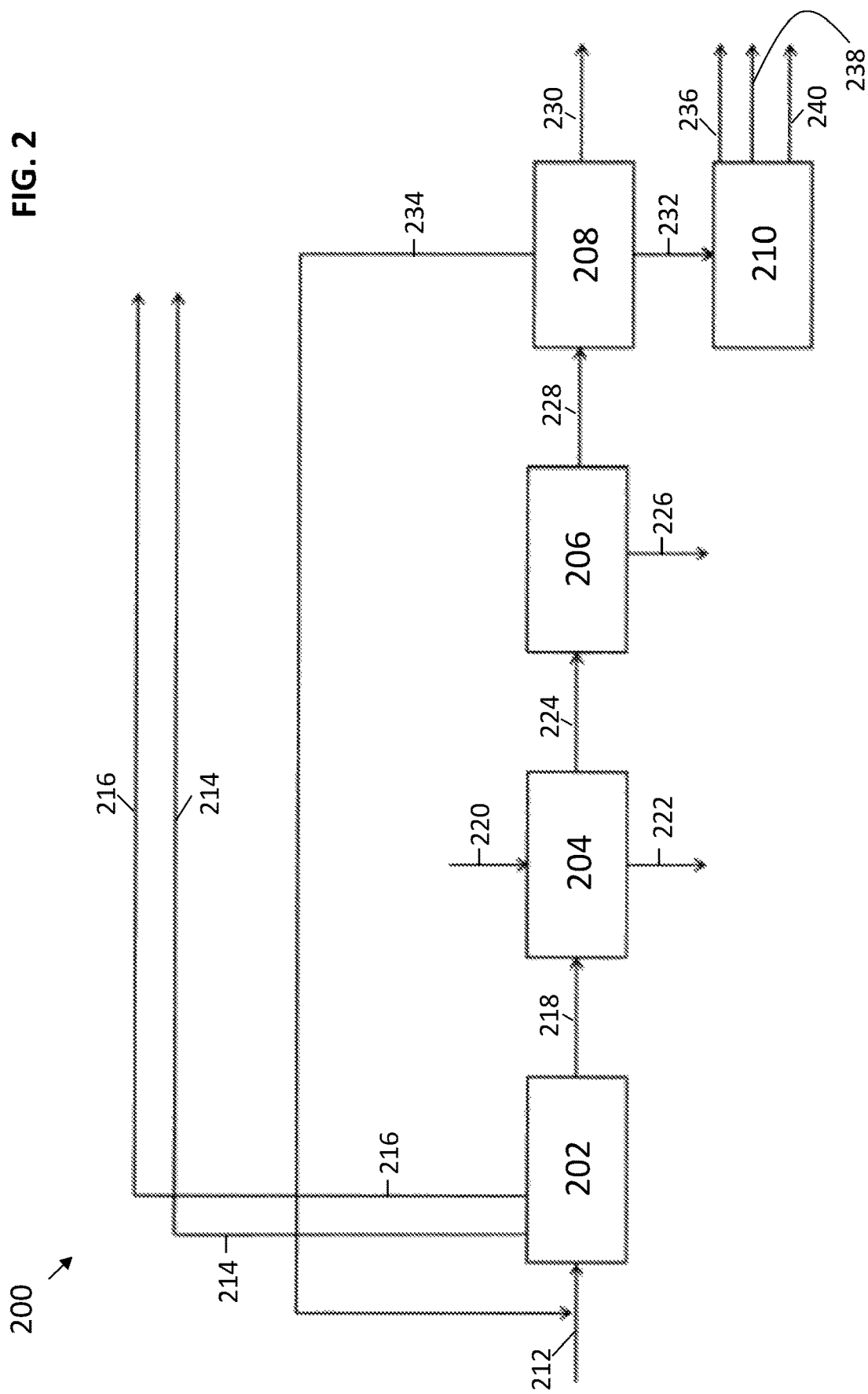

FIG. 2 provides a high-level diagram illustrating an integrated system 200 for producing isononanol and gasoline and diesel blending components in accordance with one or more embodiments of the present application. System 200 includes a steam cracker 202, an MTBE unit 204, a butadiene extraction unit 206, a isononanol (INA) unit 208, and a separation unit 210. It should be understood that the steam cracker 202 and the other units of the system 200 are fluidly connected to one another via a series of conduits or lines as shown in FIG. 2. The steam cracker 202 is configured to receive a hydrocarbon feed via conduit 212. The hydrocarbon feed can be provided from a source of hydrocarbons as is understood in the art. Typically, the hydrocarbon feed for the steam cracker 202 includes one or more hydrocarbons such as ethane, propane, butane, liquefied petroleum gas (LPG), and naphtha. The hydrocarbon feed undergoes cracking reactions in the steam cracker 202 in the presence of steam. The cracking reactions of the hydrocarbon feed generally take place in pyrolysis tubes of the steam cracker 202. In one or more embodiments, the cracking reactions takes place at high temperatures of 800-900° C. In one or more embodiments, the residence time of the hydrocarbon feed in the steam cracker 202 is 0.1-2.0 seconds.

The resulting products of the cracking reaction are a function several factors, including the hydrocarbon feedstock composition, the hydrocarbon-to-steam ratio, the cracking temperature and pressure, and the furnace residence time. In one or more embodiments, as shown in FIG. 2, the products of the cracking reaction in the steam cracker 202 are ethylene, propylene and a mixed C4 stream that can comprise butenes (e.g., isobutene, butene-1, butene-2), butanes (e.g., n-butanes, isobutane), butadiene, and pyrolysis gasoline and fuel oil. In one or more embodiments, the ethylene, propylene, and mixed C4 streams can exit the steam cracker separately. For example, as shown in FIG. 2, the ethylene stream can exit the steam cracker 202 via conduit 214, the propylene stream can exit the steam cracker 202 via conduit 216, and the mixed C4 stream can exit the steam cracker 202 via conduit 218.

In one or more embodiments the steam cracker 202 comprises multiples stages, including a cracking furnace for the primary cracking reactions. In one or more embodiments, the steam cracker 202 includes 1 or more other stages such as a quench, a downstream compression stage, a cold box, and a recovery/purification stage. The recovery/purification stage can include one or more of a demethanizer, a deethanizer, a depropanizer, and a debutanizer for separating the ethylene, propylene, and mixed C4 streams from one another before exiting the steam cracker 202 via separate conduits.

The mixed C4 stream that exits the steam cracker 202 via conduit 218 is then fed to the MTBE unit 204. The MTBE unit 204 is also configured to receive a methanol stream via conduit 220. In the MTBE unit 204, the isobutene (isobutylene) in the mixed C4 stream reacts with the methanol stream to form MTBE. The reaction of isobutene with methanol is shown below.

MTBE Production

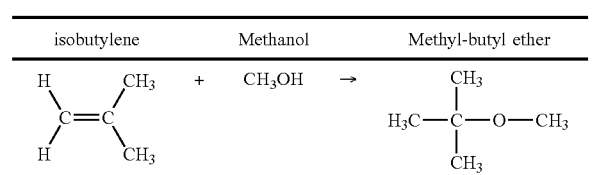

The remaining portion of the mixed C4 stream that does not react with the methanol stream is a butadiene-rich C4 stream as a result of the reactions. In one or more embodiments, the produced MTBE and the butadiene-rich C4 stream can be separated to separate streams via a series of columns in the MTBE unit 204. Additional the series of columns in the MTBE unit can also separate any unreacted methanol into a separate stream for recycling for further reactions with isobutene. In one or more embodiments, the produced MTBE can exit the MTBE unit 204 via conduit 222. Separately, the butadiene-rich C4 stream can exit the MTBE unit 204 via conduit 224.

The butadiene-rich C4 stream exiting the MTBE unit 204 via conduit 224 is then transferred to the butadiene extraction unit (BD unit) 206. In the butadiene extraction unit 206, the butadiene-rich C4 stream is reacted to extract the butadiene from the butadiene-rich C4 stream. In one or more embodiments, Butadiene is extracted from the C4 stream by solvent extraction. In one or more embodiments, the butadiene extraction process can use N-methylpyrrolidone (NMP) as a selective solvent to recover butadiene from the C4 stream. In at least one embodiment, dimethylformamide (DMF) can be used as a selective solvent for butadiene recovery. The butadiene extraction process results in a butene-rich C4 stream. In one or more embodiments, the extracted butadiene exits the extraction unit 206 via conduit 226. The butene-rich C4 stream exits the extraction unit 206 via conduit 228.

The butene-rich C4 stream exiting the extraction unit 206 via conduit 228 is then fed to the isononanol unit 208. In the isononanol unit 208, at least a portion of the butenes-rich C4 stream undergoes a series of reactions to produce an olefin-rich stream and an isononanol stream. Specifically, in one or more embodiments, the butenes of butenes-rich C4 stream undergo a dimerization reaction to form butene dimers (C8 components), including isooctene (the dimer of isobutene). At least a portion of the butene dimers (C8 components) can continue to react (oligomerize) to form further hydrocarbon oligomers, include C12 and C16 components. Exemplary dimerization reactions are shown below.
Dimerization of Butenes For example, as shown above, butene-1 can undergo a dimerization reaction to form isooctene. In one or more embodiments, butene-1 and butene-2 can undergo two-step reactions to form diisobutene (2,4,4-trimethylpent-1-ene and 2,4,4-trimethylpent-2-ene) as shown below:

Step 1: Isomerization of Butene-1, Trans-2-Butene, and Cis-2-Butene

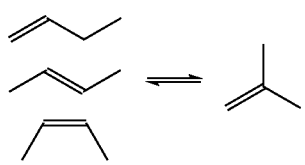

Step 2: Dimerization of Isobutene

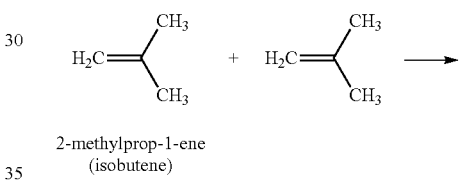

2-methylprop-1-ene
(isobutene)

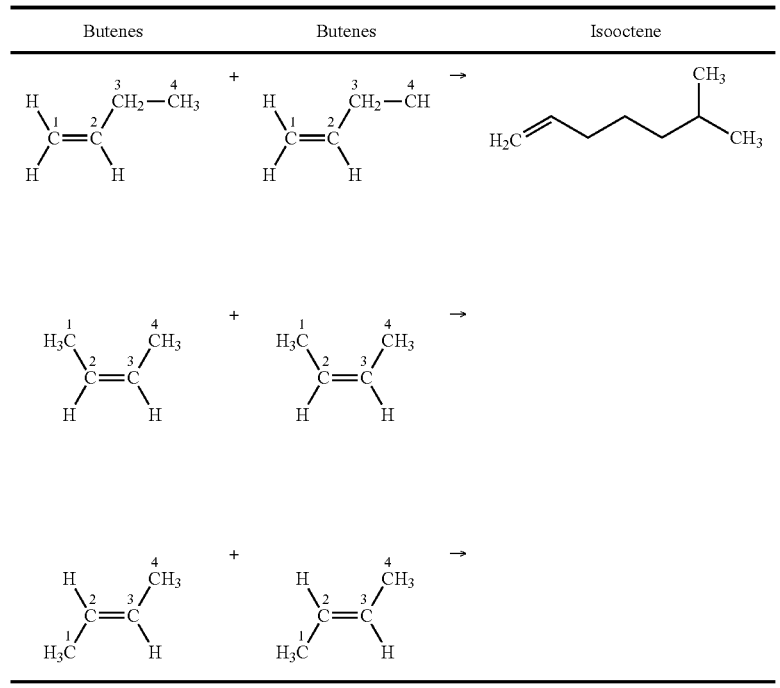

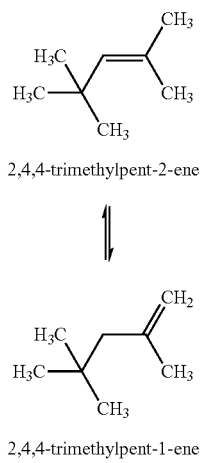

2,4,4-trimethylpent-2-ene

⇕

2,4,4-trimethylpent-1-ene

In the above 2-step reactions, butene-2 dimerization happens at slow rate compared with butene-1 dimerization. Further, in step 1, the 1-butene isomerization rate is much faster than 2-butene isomerization rate.

In one or more embodiments, the formed isooctene in the isononanol unit 208 subsequently undergoes a hydroformylation reaction with syngas (comprising carbon monoxide and hydrogen) present in the isononanol unit 208 to form isononanal. An exemplary hydroformylation reaction of isooctene and syngas is shown below.

Hydroformylation of Isooctene with Syngas

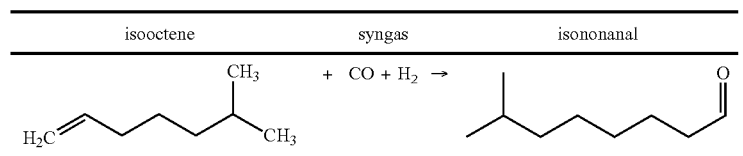

In one or more embodiments, the syngas can be produced in the furnace of the steam cracker 202 and can then be recovered in a cold box and recovery section of the steam cracker 202, for example. The produced syngas can then be transferred along with the C4 stream to the MTBE unit 204, the extraction unit 206, and eventually to the isononanol unit 208. In at least one embodiment, the syngas present in the isononanol unit 208 can be from external sources (not shown) and can then be transferred to the isononanol unit 208.

The formed isononanal undergoes a hydrogenation reaction with hydrogen of the syngas present in the isononanol unit 208 to form isononanol. An exemplary hydrogenation reaction is shown below.

Hydrogenation of Isononanal

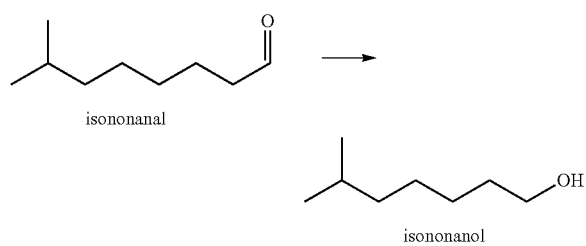

The formed isononanol exits the isononanol unit 208 via conduit 230 for collection and any further processing. The C8, C12, C16 components that remain from the dimerization and oligomerization reactions (collectively, the olefin-rich stream) exit the isononanol unit 208 via conduit 232. Any unreacted C4 components, include butenes and/or butanes, can exit the isononanol unit 208 via conduit 234. In one or more embodiments, to separate the isononanol, the C8, C12, and C16 components, and the unreacted C4 components in the isononanol unit 208, a distillation column is used. The resulting streams of C8, C12, and C16 components meet key fuel specifications for octane number (for the C8 components) and cetane number (for C12 and C16 components) as discussed in further detail below. In one or more embodiments, as shown in FIG. 2, the conduit 234 recycles the unreacted C4 components back to the steam cracker 202.

In one or more embodiments, the unreacted C4 components in the isononanol unit 208 include n-butenes and n-butanes. The formed C8 components in the isononanol unit 208 can include octene-1, n-octane, iso-octane, and n-nonanal. The formed C12 components in the isononanol unit 208 can include isomers of dodecene, along with other C12 olefins. The formed C16 components in the isononanol unit 208 can include 1-hexadecene and 1-eicosene.

The olefin-rich fuel oil stream is transferred via conduit 232 to a separation unit 210. The separation unit 210 is configured to separate the olefin-rich fuel oil stream into a C8 fuel oil steam, a C12 fuel oil stream, and a C16 fuel oil stream. The C8 fuel oil stream exits the separation unit via conduit 236, the C12 fuel oil stream exits the separation unit via conduit 238, and the C16 fuel oil stream exits the separation unit via conduit 240.

Separation of the C8, C12, and C16 components into respective fuel oil streams can be completed via one or more fractionation techniques, such as a distillation process, steam, gas or heat stripping, or flash distillation, for example. In one or more embodiments, the C8 fuel oil stream is olefinic (alkenes) in major proportion and paraffinic (alkanes) in minor proportion and therefore has sufficient octane to be utilized as a gasoline blending component. Table 1 summarizes the octane numbers of an exemplary C8 fuel oil stream, including the octane numbers for its olefinic and paraffinic portions.

| Stream | Min | Max | Average |
|---|---|---|---|
| C8 olefins (33 pure components) | 26.7 | 106.7 | 86.6 |
| C8 paraffins (36 pure components) | −18 | 117.5 | 72.6 |
| C8 mix (76 pure components) | −18 | 117.5 | 78.9 |

In one or more embodiments, the C12 and C16 fuel oil streams are also olefinic (alkenes) in major proportion and paraffinic (alkanes) in minor proportions. Accordingly, the C12 and C16 fuel streams each have sufficient cetane number to be used as diesel blending components. Table 2 summarizes the cetane number of exemplary C12 and C16 fuel oil streams, including the cetane numbers for their various components.

| Stream | Cetane Number |
|---|---|
| Dodecane (C12) | 91 |
| Dodecene (C12) | 60 |
| Hexadecane (C16) | 104 |
| Hexadecene (C16) | 87 |

As shown in Table 2, the C12 and C16 streams have very high cetane numbers such that they are useful as blending components to diesel fuels. It should be noted that the required cetane number (cetane rating) for diesel fuel varies throughout the world but is generally in the range 40-53.

Figure 3:
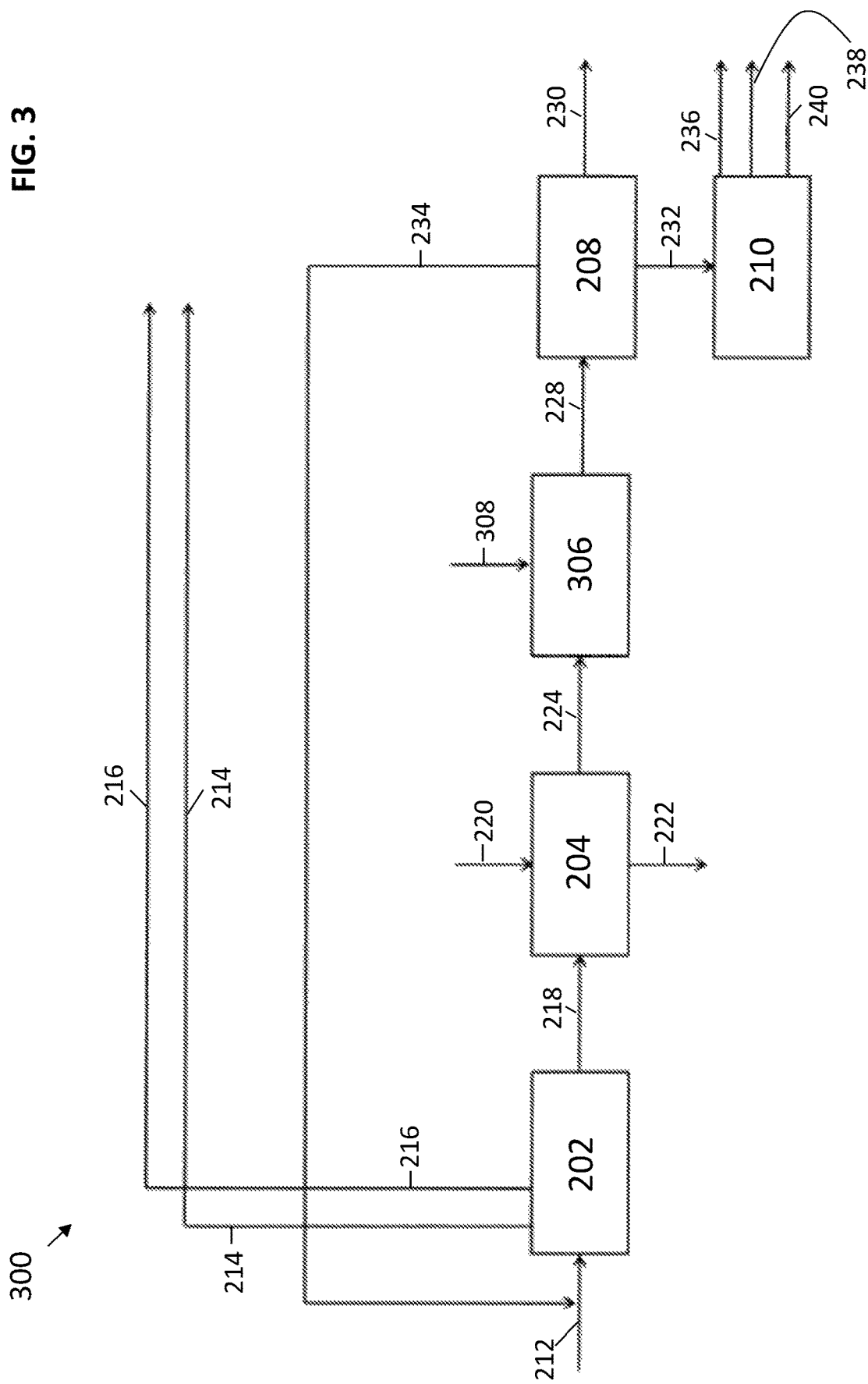

FIG. 3 shows another high-level diagram illustrating an integrated system for producing isononanol and gasoline and diesel blending components in accordance with one or more embodiments of the present application. In particular, the system 300 is similar to the system 200 of FIG. 2, except that the butadiene extraction unit 206 of system 200 is replaced by a butadiene selective hydrogenation unit 306. The operations of the steam cracker 202 and the MTBE unit 204 of system 300 are the same as their respective counterparts in system 200 of FIG. 2. Like the butadiene extraction unit 206 in system 200, the butadiene selective hydrogenation unit (BD SHU) 306 in system 300 receives the butadiene-rich C4 stream from the MTBE unit 202 via conduit 224. The butadiene selective hydrogenation unit 306 also receives a stream of hydrogen gas via conduit 308. The butadiene (1,3 butadiene) in the butadiene-rich C4 stream is then selectively hydrogenated in the BD SHU 306 with the hydrogen stream to form a butene-rich C4 stream, which include butene-1, cis-butene-2, and trans-butene-2. The selective hydrogenation reaction of butadiene is shown below:

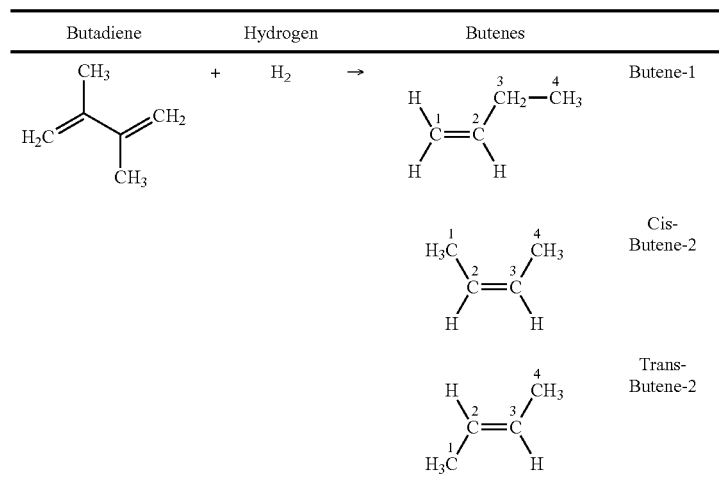

The butene-rich C4 stream formed via the selective hydrogenation reaction is then transferred to the isononanol unit 208 via line 228. The remaining operations of the isononanol unit 208 and the separation unit 210 in system 300 are substantially the same as described above for their respective counterparts in system 200 of FIG. 2.

Figure 4:
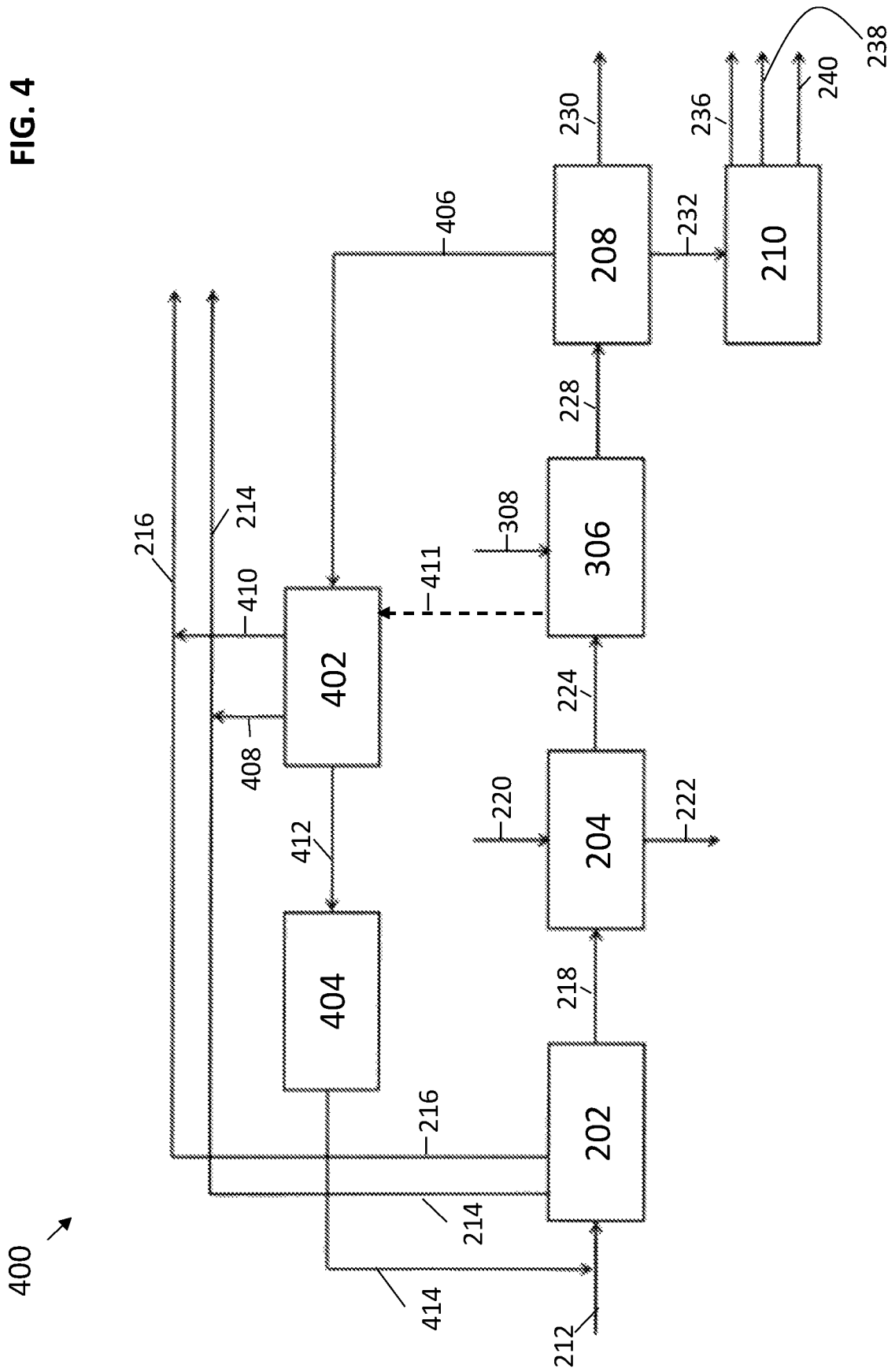

FIG. 4 shows a high-level diagram illustrating another embodiment of the integrated system for producing isononanol and gasoline and diesel blending components. In particular, FIG. 4 displays a system 400 that includes all the components of system 300 in FIG. 3, as well as two additional units—a C4 metathesis unit 402 and C4 hydrogenation unit 404. In system 400, instead of the unreacted C4 components (e.g., butenes, butanes) in the isononanol unit 208 being recycled directly back to the steam cracker 202, the unreacted C4 components are first transferred to the C4 metathesis unit 402 via conduit 406. In the C4 metathesis unit 402, the unreacted C4 components—in particular, butenes—undergo a metathesis reaction to produce an ethylene stream and a propylene stream. For example, in one or more embodiments, the C4 metathesis unit 402 can be a self-metathesis unit in which the self-metathesis process is generally a two-step process: 2-butene isomerization and then cross-metathesis using a metathesis catalyst system, as shown in following formulas.

2-Butene Isomerization

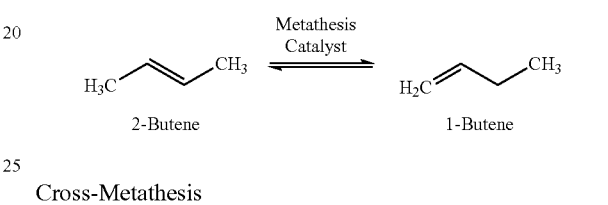

Cross-Metathesis

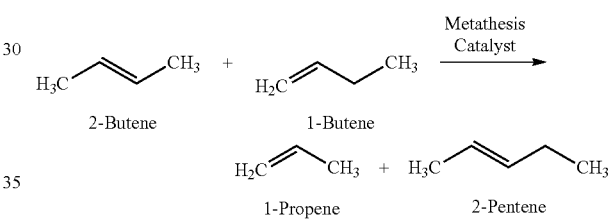

-continued

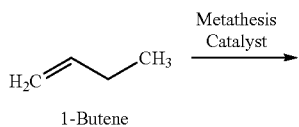

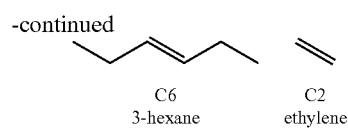

C6
3-hexane

C2
ethylene

In at least one embodiment, the C4 metathesis unit 402, can further comprises a catalytic cracking reaction of 2-pentene as shown by the following equation.

Catalytic Cracking

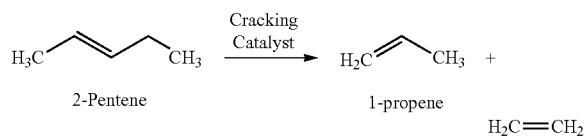

2-Pentene 1-propene $H_2C = CH_2$

In at least one embodiment, the C4 metathesis unit 402 is the metathesis reactor shown and described in U.S. Pat. No. 10,214,466, which is hereby incorporated by reference incorporated by reference as if set forth in its entirety herein. In at least one embodiment, the C4 metathesis unit 402 is a traditional C4 metathesis unit.

With continued reference to FIG. 4 and as shown in the above equations, the unreacted C4 components (e.g., butenes, butanes) act as the metathesis feed for the reactions in the C4 metathesis unit 402 to produce propylene and ethylene. The ethylene stream exits the C4 metathesis unit 402 via conduit 408 and the propylene (propene) stream exits the C4 metathesis unit 402 via conduit 410.

As shown in FIG. 4, in one or more embodiments the conduit 408 is fluidly connected to conduit 214 such that the ethylene stream produced in the C4 metathesis unit 402 is combined with the ethylene stream produced in the steam cracker 202. The combined stream of ethylene can then be transported via conduit 214 for further processing. Similarly, as shown in FIG. 4, in one or more embodiments the conduit 410 is fluidly connected to conduit 216 such that the propylene stream produced in the C4 metathesis unit 402 is combined with the propylene stream produced in the steam cracker 202. The combined stream of propylene can then be transported via conduit 216 for further processing.

In at least one embodiment, a C4 stream (e.g., 48 weight % raffinate-2) can fed directly from the butadiene selective hydrogenation unit 306 directly to the C4 metathesis unit 402 via conduit 411 to increase the yield of propylene and ethylene. In at least one such embodiment, the combined production of propylene and ethylene can be increased to 240 KTA, while still maintaining an increase in isononanol production as compared with conventional systems.

A portion of C4 components that remain unreacted in the C4 metathesis unit 402—predominantly butenes—exits the C4 metathesis unit 402 via conduit 412 and is transferred to a C4 hydrogenation unit 404. In the C4 hydrogenation unit 404, the butenes are hydrogenated to form a butanes stream. The butanes stream then exits the C4 hydrogenation unit 404 via conduit 414, which recycles the butanes back to the steam cracker 202. In at least one embodiment of system 400, the butadiene selective hydrogenation unit 306 can be replaced with a butadiene extraction unit. In such an embodiment, the butadiene extraction unit would operate in substantially the same manner as the butadiene extraction unit 206 operates in system 200 of FIG. 2. It should be understood that the steam cracker 202, the MTBE 204, BD SHU 306, isononanol unit 208, and separation unit 210 in system 400 of FIG. 4 operate in substantially the same manner as described above in the description of systems 200 (FIG. 2) and 300 (FIG. 3).

The systems and methods of the present application provide several improvement over previous systems and methods for producing isononanol. In particular, the present systems and methods separate the olefin-rich fuel oil stream from the isononanol unit—which has little standalone value—into separate C8, C12, and C16 fuel oil streams, which are valuable gasoline and/or diesel blending additives. Further, the present systems and methods provide increased isononanol yield as compared with conventional systems. This increased isononanol yield is shown in the following examples, which refers to FIGS. 5A, 5B, 6, and 7.

Example 1

This example shows the isononanol yield difference between the conventional system shown in FIG. 1 and an embodiment of the present application shown in FIG. 3. In this example, a 500 kilotons per annum (KTA) hydrocarbon feed is used, where the feed mainly consists of C4 hydrocarbons. The components of the hydrocarbon feed are shown in weight % (W %) in the table of FIG. 5A, along with the range of a typical hydrocarbon feed for the present systems. FIG. 5B displays a table showing the differences in yields of various products between the conventional system of FIG. 1 and the embodiment of system 200 of FIG. 3 of the present application. As shown in the table of FIG. 5B, the embodiment of the present application shown in FIG. 3 results in a more than 3-fold increase in isononanol yield as compared with the conventional system of FIG. 1 (588 KTA vs. 158 KTA). This increase in isononanol yield is due, at least in part, to the conversion of butadiene to butene-2, cis-butene-2, and trans-butene-2 in the butadiene selective hydrogenation unit.

Additionally, the embodiment of FIG. 3 also results in a substantial increase in the yield of C8-C16 fuel oil streams as compared with the conventional system of FIG. 1 (74 KTA vs. 21 KTA). Further, because the present systems, as exemplified in FIG. 3, provide separation of the C8-C16 stream into separate C8, C12, and C16 fuel oil streams, the present systems provide even greater value for these components as gasoline and/or diesel blending additives.

Example 2

In this example, a 1000 KTA mixed C4 feed (FIG. 1, conduit 5; FIG. 3, conduit 218) from the steam cracker is used downstream in the subsequent units of the systems FIG. 1 and FIG. 3, respectively. FIG. 6 shows a table displaying the composition of the various streams of the convention system of FIG. 1, FIG. 7 shows a table displaying the composition of the various streams of the system of FIG. 2, and FIG. 8 shows a table displaying the composition of the various streams of the system of FIG. 3 in accordance with one or more embodiments. The tables of FIGS. 6, 7, and 8 are organized by the conduits (lines) shown in FIGS. 1, 2, and 3, respectively.

As shown in FIGS. 6 and 8, the embodiment of FIG. 3 results in a more than 3-fold increase in isononanol yield as compared with the conventional system of FIG. 1 (FIG. 1, conduit 11: 158 KTA vs. FIG. 2, conduit 230: 558 KTA). Additionally, the embodiment of FIG. 3 also results in a substantial increase in the yield of C8-C16 fuel oil streams as compared with the conventional system of FIG. 1 (FIG. 1, conduit 12: 41 KTA; FIG. 3, conduits 236-240: 147 KTA).

Accordingly, as discussed herein and as shown in the above examples, the present systems and methods for producing isononanol and gasoline and diesel blending components provide substantial increases in the yield of isononanol as compared with conventional systems. Further, the present systems provide increased yields of C8, C12, and C16 fuel components relative to conventional systems, and also separate the C8, C12, and C16 fuel components into individual streams such that they are more valuable as individual gasoline blending components (C8 fuel components) and diesel blending components (C12, C16 fuel components), respectively. In one or more embodiments, the present systems and methods also provided increase yield of ethylene and propylene as compared with conventional systems.

Although much of the foregoing description has been directed to systems and methods for producing isononanol and gasoline and diesel blending components, the system and methods disclosed herein can be similarly deployed and/or implemented in scenarios, situations, and settings far beyond the referenced scenarios. It should be further understood that any such implementation and/or deployment is within the scope of the system and methods described herein.

It is to be further understood that like numerals in the drawings represent like elements through the several figures, and that not all components and/or steps described and illustrated with reference to the figures are required for all embodiments or arrangements. Further, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "including," "comprising," or "having," "containing," "involving," and variations thereof herein, when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Notably, the figures and examples above are not meant to limit the scope of the present disclosure to a single implementation, as other implementations are possible by way of interchange of some or all of the described or illustrated elements. Moreover, where certain elements of the present disclosure can be partially or fully implemented using known components, only those portions of such known components that are necessary for an understanding of the present disclosure are described, and detailed descriptions of other portions of such known components are omitted so as not to obscure the disclosure. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present disclosure encompasses present and future known equivalents to the known components referred to herein by way of illustration.

The foregoing description of the specific implementations will so fully reveal the general nature of the disclosure that others can, by applying knowledge within the skill of the relevant art(s) (including the contents of the documents cited and incorporated by reference herein), readily modify and/or adapt for various applications such specific implementations, without undue experimentation, without departing from the general concept of the present disclosure. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s). It is to be understood that dimensions discussed or shown are drawings are shown accordingly to one example and other dimensions can be used without departing from the disclosure.

The subject matter described above is provided by way of illustration only and should not be construed as limiting. Various modifications and changes can be made to the subject matter described herein without following the example embodiments and applications illustrated and described, and without departing from the true spirit and scope of the invention encompassed by the present disclosure, which is defined by the set of recitations in the following claims and by structures and functions or steps which are equivalent to these recitations.

What is claimed is:

1. A system for production of isononanol and gasoline and diesel blending components, the system comprising:
    a steam cracker configured to receive a hydrocarbon feed, wherein the hydrocarbon feed comprises C1-C4 olefins and naphtha, and wherein the hydrocarbon feed undergoes a cracking reaction to form a first ethylene stream, a first propylene stream, and a C4 stream comprising isobutene and butadiene;
    a methyl tertiary butyl ether (MTBE) unit fluidly connected to the steam cracker, wherein the MTBE unit is configured to receive a methanol stream and to receive the C4 stream from the steam cracker, and wherein the isobutene in the C4 stream reacts with the received methanol to form MTBE, and wherein the remaining C4 stream is a butadiene-rich C4 stream;
    a butadiene unit fluidly connected to the MTBE unit, wherein the butadiene unit is configured to receive the butadiene-rich C4 stream from the MTBE unit and wherein the butadiene-rich C4 stream is reacted in the butadiene unit to form a butene-rich C4 stream;
    an isononanol unit fluidly connected to the butadiene unit, wherein the isononanol unit is configured to receive the butene-rich C4 stream and wherein a portion of the butene-rich C4 stream undergoes a series of reactions to form an olefin-rich stream and an isononanol stream; and
    a separation unit fluidly connected to the isononanol unit, wherein the separation unit is configured to receive the olefin-rich stream and wherein the olefin-rich stream is separated into a C8 fuel oil steam, a C12 fuel oil stream, and a C16 fuel oil stream.

2. The system of claim 1, wherein the butadiene unit is a butadiene extraction unit, and wherein the butadiene extraction unit is configured to separate butadiene from the butadiene-rich C4 stream to form the butene-rich C4 stream.

3. The system of claim 1, wherein the series of reactions in the isononanol unit include dimerization and oligomerization of butenes to form butene dimers including isooctene, and other C8, C12, and C16 components, which form the olefin-rich stream, hydroformylation of isooctene with syngas to form isononanal, and hydrogenation of isononanal to form isononanol.

4. The system of claim 1, wherein the first ethylene stream, the first propylene stream, and the C4 stream each exit the steam cracker via separate conduits.

5. The system of claim 1, wherein the series of reactions in the isononanol unit results in a stream of unreacted C4 olefins, and wherein the system further comprises:
a recycling conduit configured to recycle the stream of unreacted C4 olefins to the steam cracker.

6. A system for production of isononanol and gasoline and diesel blending components, the system comprising:
a steam cracker configured to receive a hydrocarbon feed, wherein the hydrocarbon feed undergoes a cracking reaction to form a first ethylene stream, a first propylene stream, and a C4 stream comprising isobutene and butadiene;
a methyl tertiary butyl ether (MTBE) unit fluidly connected to the steam cracker, wherein the MTBE unit is configured to receive a methanol stream and to receive the C4 stream from the steam cracker, and wherein the isobutene in the C4 stream reacts with the received methanol to form MTBE, and wherein the remaining C4 stream is a butadiene-rich C4 stream;
a butadiene selective hydrogenation unit fluidly connected to the MTBE unit, wherein the butadiene selective hydrogenation unit is configured to receive the butadiene-rich C4 stream from the MTBE unit and a hydrogen stream, and the butadiene-rich C4 stream undergoes a selective hydrogenation reaction with the hydrogen stream to form butene-1, cis-butene-2, and trans-butene-2;
an isononanol unit fluidly connected to the butadiene selective hydrogenation unit, wherein the isononanol unit is configured to receive the butene-rich C4 stream and wherein a portion of the butene-rich C4 stream undergoes a series of reactions to form an olefin-rich stream and an isononanol stream;
a separation unit fluidly connected to the isononanol unit, wherein the separation unit is configured to receive the olefin-rich stream and wherein the olefin-rich stream is separated into a C8 fuel oil steam, a C12 fuel oil stream, and a C16 fuel oil stream;
a C4 metathesis unit, wherein the C4 metathesis unit is configured to receive a stream of unreacted C4 olefins from the butene-rich C4 stream in the isononanol unit and wherein a first portion of the stream of unreacted C4 olefins undergoes a metathesis reaction to produce a second ethylene stream and a second propylene stream; and a C4 hydrogenation unit configured to receive a second portion of the stream of unreacted C4 olefins from the C4 metathesis unit, and wherein the second portion of unreacted C4 olefins undergoes a hydrogenation reaction to form butanes, and wherein the C4 hydrogenation unit is configured to transfer the formed butanes back to the steam cracker.

7. The system of claim 6, wherein the second ethylene stream is combined with the first ethylene stream via a first conduit and the second propylene stream is combined with the first propylene stream via a second conduit.

8. A system for production of isononanol and gasoline and diesel blending components, the system comprising:
a steam cracker configured to receive a hydrocarbon feed, wherein the hydrocarbon feed undergoes a cracking reaction to form a first ethylene stream, a first propylene stream, and a C4 stream comprising isobutene and butadiene;
a methyl tertiary butyl ether (MTBE) unit fluidly connected to the steam cracker, wherein the MTBE unit is configured to receive a methanol stream and to receive the C4 stream from the steam cracker, and wherein the isobutene in the C4 stream reacts with the received methanol to form MTBE, and wherein the remaining C4 stream is a butadiene-rich C4 stream;
a butadiene unit fluidly connected to the MTBE unit, wherein the butadiene unit is configured to receive the butadiene-rich C4 stream from the MTBE unit and wherein the butadiene-rich C4 stream is reacted in the butadiene unit to form a butene-rich C4 stream;
an isononanol unit fluidly connected to the butadiene unit, wherein the isononanol unit is configured to receive the butene-rich C4 stream and wherein a portion of the butene-rich C4 stream undergoes a series of reactions to form an olefin-rich stream and an isononanol stream, wherein the series of reactions in the isononanol unit results in a stream of unreacted C4 olefins;
a separation unit fluidly connected to the isononanol unit, wherein the separation unit is configured to receive the olefin-rich stream and wherein the olefin-rich stream is separated into a C8 fuel oil steam, a C12 fuel oil stream, and a C16 fuel oil stream; and
a recycling conduit configured to recycle the stream of unreacted C4 olefins to the steam cracker.

9. The system of claim 8, wherein the series of reactions in the isononanol unit include dimerization and oligomerization of butenes to form butene dimers including isooctene, and other C8, C12, and C16 components, which form the olefin-rich stream, hydroformylation of isooctene with syngas to form isononanal, and hydrogenation of isononanal to form isononanol.

10. The system of claim 8, wherein the butadiene unit is a butadiene extraction unit, and wherein the butadiene extraction unit is configured to separate butadiene from the butadiene-rich C4 stream to form the butene-rich C4 stream.

* * * * *